United States Patent [19]

Kimrey, Jr. et al.

[11] Patent Number: 5,099,096
[45] Date of Patent: Mar. 24, 1992

[54] MICROWAVE FURNACE HAVING MICROWAVE COMPATIBLE DILATOMETER

[75] Inventors: Harold D. Kimrey, Jr.; Mark A. Janney, both of Knoxville; Mattison K. Ferber, Oak Ridge, all of Tenn.

[73] Assignee: Martin Marietta Energy Systems, Inc., Oak Ridge, Tenn.

[21] Appl. No.: 505,371

[22] Filed: Apr. 5, 1990

[51] Int. Cl.⁵ .................. H05B 6/68; G01N 25/16
[52] U.S. Cl. ................. 219/10.55 B; 219/10.55 R; 374/55; 374/56
[58] Field of Search .......... 219/10.55 B, 10.55 R, 219/10.55 A, 10.55 E, 10.55 F, 10.55 D, 518; 374/55, 56; 264/27, 25, 26

[56] References Cited

U.S. PATENT DOCUMENTS

| | | |
|---|---|---|
| 2,336,286 | 12/1943 | Owen . |
| 2,478,895 | 8/1949 | Christenson et al. ............ 374/56 |
| 3,295,358 | 1/1967 | Boenisch . |
| 3,585,258 | 6/1971 | Levinson ............... 219/10.55 R |
| 3,726,125 | 4/1973 | Heyman . |
| 4,057,702 | 11/1977 | Lacombe-Allard ......... 219/10.55 A |
| 4,100,386 | 7/1978 | Bardet . |
| 4,147,911 | 4/1979 | Nishitani .............. 219/10.55 M |
| 4,163,140 | 7/1979 | Bardet ............... 219/10.55 B |
| 4,189,629 | 2/1980 | Kraze ............... 219/10.55 A |
| 4,307,277 | 12/1981 | Maeda et al. .......... 219/10.55 R |
| 4,313,679 | 2/1982 | Wolff et al. ............ 219/10.67 |
| 4,323,745 | 4/1984 | Berggen ............. 219/10.55 A |
| 4,529,856 | 7/1985 | Meek et al. .......... 219/10.55 M |
| 4,529,857 | 7/1985 | Meek et al. .......... 219/10.55 M |
| 4,548,515 | 10/1985 | Clusener .................. 374/56 |
| 4,559,429 | 12/1985 | Holcombe ............ 219/10.55 F |
| 4,565,669 | 1/1986 | Collins et al. ......... 219/10.55 R |
| 4,618,274 | 10/1986 | Clusener ................... 374/55 |
| 4,636,969 | 1/1987 | Kyoden et al. ............... 374/55 |
| 4,683,363 | 7/1987 | Scovell .............. 219/10.55 A |
| 4,743,340 | 5/1988 | Wrenn, Jr. et al. . |
| 4,762,424 | 8/1988 | Baricevac et al. ............ 374/56 |
| 4,764,102 | 8/1988 | Takahashi ........... 219/10.55 R |
| 4,771,153 | 9/1988 | Fukushima et al. ...... 219/10.55 B |
| 4,784,686 | 11/1988 | Meek et al. .................. 34/4 |
| 4,808,780 | 2/1989 | Seaborne ............. 219/10.55 F |
| 4,810,846 | 3/1989 | Holcombe et al. ........ 219/10.55 R |
| 4,831,239 | 5/1989 | Ueda ................ 219/10.55 B |
| 4,880,578 | 11/1989 | Holcombe et al. ............ 264/26 |

FOREIGN PATENT DOCUMENTS

| | | | |
|---|---|---|---|
| 330933 | 9/1989 | European Pat. Off. ........... 374/55 |
| 2565348 | 12/1985 | France .................. 374/55 |

OTHER PUBLICATIONS

C. E. Holcombe and N. L. Dykes, "High-Temperature Microwave Sintering of Nonoxide Ceramics," *91st Annual Meeting of the American Ceramics Society*, Apr. 25, 1989, discusses microwave sintering of nonoxide ceramics.
C. E. Holcombe, T. T. Meek, and N. L. Dykes "Unusual Properties of Microwave-Sintered Yttria-2 wt. % Firconia," *J. Nat'l Sc. Letters*, 7, 881–884 (1988).
C. E. Holcombe, T. T. Meek, and N. L. Dykes "Enhanced Thermal Shock Properties of $Y_2O_3$-2 wt. %$ZrO_2$ Heated Using 2.45 GHz Radiation," *Mat. Res. Soc. Symp. Proc.*, vol. 124, Apr. 5–8 (1988) discusses Yttrium-2 w/o Zirconia heated by 2.45 GHz radiation.
W. H. Sutton, "Microwave Processing of Ceramic Materials," *Ceramic Bulletin*, vol. 68, No. 2, 376–286 (1989) discusses microwave processing of ceramic materials.
C. E. Holcombe, "New Microwave Coupler Material", *Am. Ceram. Soc. Bulletin*, vol. 62, 1388 (1983) discusses coupler material for microwave applications.

*Primary Examiner*—Philip H. Leung
*Attorney, Agent, or Firm*—J. Donald Griffin; Harold W. Adams

[57] ABSTRACT

An apparatus for measuring and monitoring a change in the dimension of a sample being heated by microwave energy is described. The apparatus comprises a microwave heating device for heating a sample by microwave energy, a microwave compatible dilatometer for measuring and monitoring a change in the dimension of the sample being heated by microwave energy without leaking microwaves out of the microwave heating device, and a temperature determination device for measuring and monitoring the temperature of the sample being heated by microwave energy.

12 Claims, 2 Drawing Sheets

MICROWAVE FURNACE HAVING MICROWAVE COMPATIBLE DILATOMETER

This invention was made with Government support under contract DE-AC05-84OR21400 awarded by the U.S. Department of Energy to Martin Marietta Energy Systems Inc. and the Government has certain rights in this invention.

FIELD OF THE INVENTION

This invention relates to a dilatometer. More particularly, this invention relates to a microwave compatible dilatometer.

BACKGROUND OF THE INVENTION

Recently, it has been discovered that ceramic materials can be sintered in a microwave field at temperatures substantially below those needed in a conventional thermal field. Because of this recent development there is a significant need to be able to determine the sintering behavior of these materials and to monitor the dimensional changes during the microwave sintering process. However, to monitor and measure the dimensional changes during the microwave sintering process a dilatometer which is compatible to a microwave furnace is required.

Typically dilatometers have a variable temperature furnace in which the test specimen rests between a flat surface and a movable object, such as a ceramic push rod, that extends outside the furnace. Temperature induced changes in the length of the specimen are transmitted through the rod to a mechanical, optical or electrical system for amplifying and measuring that change. These instruments can be used to make precise measurements of changes in length resulting from small temperature changes or to plot variations in the rate of linear expansion or contraction over a broad temperature range.

Among the least sophisticated dilatometers in common use are those in which the push rod is coupled to a dial gauge and the dilation of a specimen is read directly from the gauge. Such dial gauge dilatometers are simple to use and inexpensive, but generally are suitable only for applications that do not demand great precision.

A far more precise type of dilatometer is one in which the dilation sensor is a linear variable differential transducer which translates specimen dilation into electrical signals that can readily be amplified and recorded. In such a sensor, the core floats freely in the coil and each of these elements is separately supported at its ends by a pair of compound cantilevered springs. These springs permit independent and frictionless axial movement of the suspended element, but restrain radial or transverse movement. This independent and frictionless axial mobility of the core and coil facilitates calibration of the sensor and renders it extremely sensitive to minute changes in specimen length, thereby making possible exceptionally accurate measurements of expansion or contraction. However, the dilatometers described above are not microwave compatible. Therefore, to monitor and measure dimensional changes of a ceramic sample during a sintering process in which the sample was heated by microwave energy, it was necessary to develop a microwave compatible dilatometer.

SUMMARY OF THE INVENTION

In accordance with one aspect of the present invention, a new and improved apparatus for monitoring and measuring dimensional changes of a sample during a microwave sintering process comprises a heating device for heating a sample by microwave energy, a microwave compatible dilatometer for measuring and monitoring a change in the dimension of the sample being heated by microwave energy without leaking microwaves out of the heating device, and a temperature determination device for measuring and monitoring the temperature of the sample being heated by microwave energy without leaking microwaves out of the heating device.

For a better understanding of the present invention, together with other and further objects, advantages and capabilities thereof, reference is made to the following disclosure and appended claims in connection with the above-described drawing.

DETAILED DESCRIPTION OF THE PREFERRED EMBODIMENTS

Figure 1:
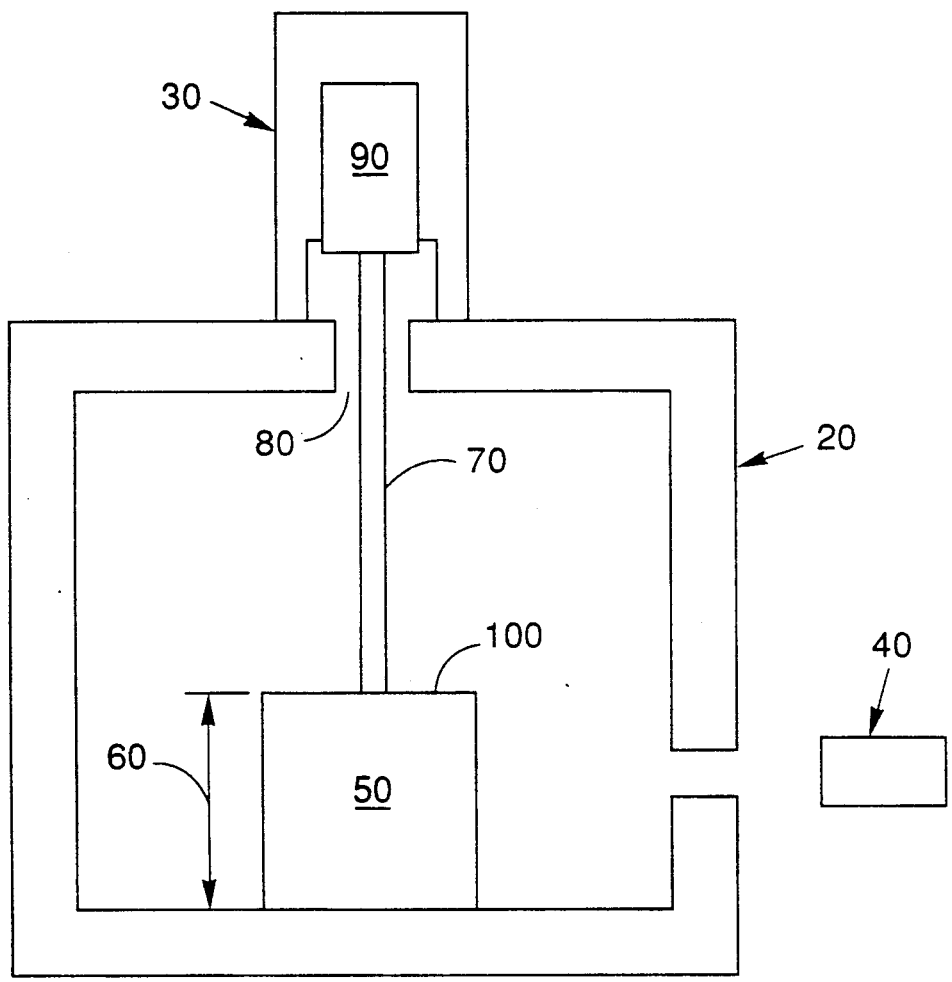
FIG. 1 is a cross-sectional view of a microwave compatible dilatometer in combination with a microwave furnace in accordance with the present invention.

Referring now to the drawing with greater particularity, there is shown in the FIG. 1 apparatus 10 which comprises, heating device 20, microwave compatible dilatometer 30, temperature determination device 40, and sample 50. Microwave compatible dilatometer 30 detects and measures a change in dimension 60 of sample 50 while being heated by microwave energy. Heating device 20, such as a microwave furnace, for heating sample 50 by microwave energy is adapted to receive movable sample contact device 70 of microwave compatible dilatometer 30 through aperture 80. Aperture 80 has a diameter sufficiently small to prevent leakage of microwaves from heating device 20 through aperture 80 when movable sample contact device 70 is located as indicated in FIG. 1. Movable sample contact device 70 is made from essentially microwave transparent materials, such as alumina. Temperature determination device 40, such as an optical pyrometer, is used to monitor and measure the temperature of the sample while being heated by microwave energy.

Microwave compatible dilatometer 30 comprises a linear variable differential transducer 90 and movable sample contact device 70, such as a ceramic push rod. One end of movable sample contact device 70 is connected to linear variable differential transducer 90 and the other end is in contact with surface 100 of sample 50.

When sample 50 is heated by microwave energy to a temperature sufficient to change dimension 60 of sample 50, the change in dimension 60 is transferred by movable sample contact device 70 to linear variable differential transducer 90 of microwave compatible dilatometer 30. The change in dimension 60 is monitored and measured by microwave compatible dilatometer 30.

Movable sample contact device 70 is made from a nonmetallic material, such as alumina, boron nitride, and has a diameter less than the diameter of aperture 80 of heating device 20.

Figure 2:
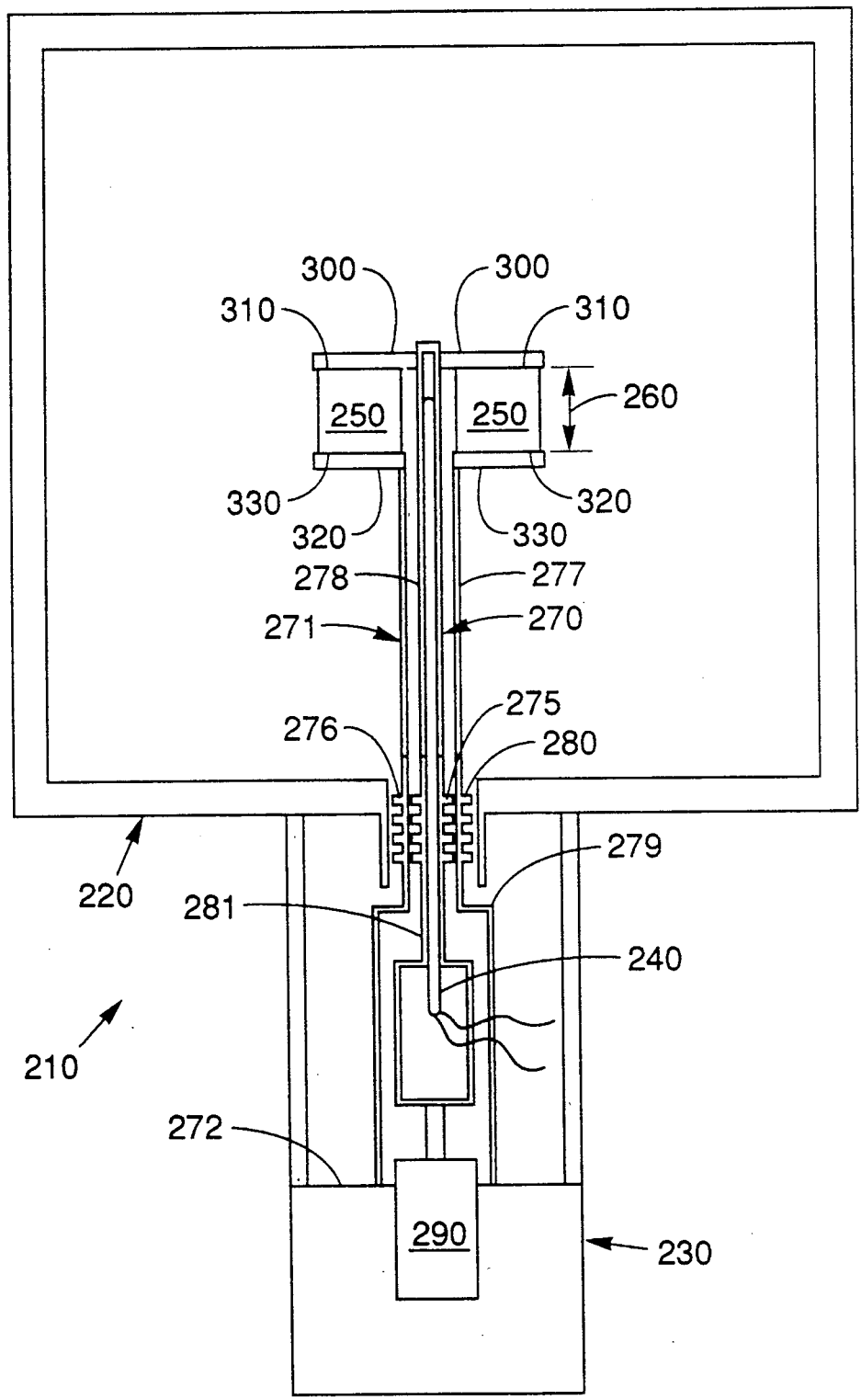
FIG. 2 is a cross-sectional view of another embodiment of a microwave compatible dilatometer in combination with a microwave furnace in accordance with the present invention.

Shown in FIG. 2 is another embodiment of the present invention. Apparatus 210 comprises, microwave heating device 220, microwave compatible dilatometer 230, temperature monitoring device 240, and sample 250. Microwave compatible dilatometer 230 monitors and measures changes in dimension 260 of sample 250 during the heating of sample 250 by microwave energy. Microwave heating device 220, such as a microwave furnace, is adapted to receive through aperture 280 of microwave heating device 220 outer push rod 271, inner push rod 270, and temperature monitoring device 240 of microwave compatible dilatometer 230 as depicted in FIG. 2. Outer push rod 271 and inner push rod 270 are concentric axial hollow rods having an upper portion and a lower portion. The concentric tube design of outer push rod 275 and inner push rods 276 accommodates temperature monitoring device 240 and only one aperture which penetrates the microwave chamber. Upper portion 277 of outer push rod 271 and upper portion 278 of inner push rod 270 are made of a ceramic material and lower portion 279 of outer push rod 271 and lower portion 281 of inner push rod 270 are made of stainless steel.

Microwave compatible dilatometer 230 comprises a linear variable differential transducer (LVDT) 290, inner push rod 270 which has a microwave bandstop choke 275 on lower portion 281 of inner push rod 270, outer push rod 271 which has a microwave bandstop choke 276 on the lower portion 279 of outer push rod 271, and temperature monitoring device 240, such as a thermocouple which is used to monitor and measure the temperature of the sample during the microwave heating and sintering cycle. Microwave bandstop chokes 275 and 276 act like microwave shields which prevent microwave energy, such as, but not limited to, 2.45 GHz or 28 GHz sources, from leaking out of microwave heating device 220 through 280.

Lower portion 281 of inner push rod 270 is connected to linear variable differential transducer 290 and upper portion 278 of inner push rod 270 is connected to first cap 300 which is in contact with first surface 310 of sample 250. Upper portion 279 of outer push rod 271 is connected to second cap 320 which is in contact with second surface 330 of sample 250 which is parallel to first surface 310 and lower portion 279 of outer push rod 271 is connected to frame 272 of microwave compatible dilatometer 230.

When sample 250 is heated by microwave energy to a temperature sufficient to change dimension 260 of sample 250, the change in dimension 260 is transferred by inner push rod 270 to linear variable differential transducer 290 of microwave compatible dilatometer 230. The change in dimension 260 is monitored and measured by microwave compatible dilatometer 230.

Outer push rod 271 has as a diameter less than the diameter of aperture 280 of microwave heating device 220.

Outer push rod 271 supports sample 250 and inner push rod 270 is supported by sample 250. Caps 300 and 320 are shaped to maximize thermal resistance between push rods 270 and 271 and sample 250. Outer push rod 271 is arranged concentrically around inner push rod 270 and inner rod 270 is arranged concentricity around temperature monitoring device 240, such as a metal sheathed thermocouple. This feature makes it possible for the temperature of sample 250 to be monitored while being heated directly by the microwave field. Upper portions 277 and 278 of push rods 270 and 271 and caps 00 and 320 are made of a ceramic material which does not significantly couple to the microwave field. The choices of materials for caps 300 and 320 include but are not limited to boron nitride and aluminum oxide.

Inner push rod 270 serves to transmit mechanical motion to liner variable differential transducer (LVDT) 290 and both inner and outer push rods 270 and 271 contain microwave filters, microwave bandstop chokes, 275 and 276 to keep the microwave energy from leaking out of microwave heating device 220 into microwave compatible dilatometer 230 which contains sensitive LVDT elements. Microwave bandstop chokes 275 and 276 are made of one quarter wavelength coaxial sections which alternate as low and high impedance waveguides. These sections cause the microwave energy to interfere destructively and to be reflected back into microwave heating device 220. By replacing the push rods 270 and 271 and thermocouple the dilatometer can be made to operate in a wide variety of atmospheres or vacuum. Both push rods are connected below and out of the microwave field by a common water cooled base plate. The push rods then see a common thermal gradient. Error in the measurement will not result from the push rods as they will expand and contract together. The error will be limited to the difference in expansion coefficients between the sample under test and the inner push rod. The stainless steel portions of the push rods which act as microwave filters for shielding the dilatometer from microwaves work best if they are very tightly spaced to one another. On the other hand, if they touch they will not work effectively. Also, it is best if the push rods do not touch so as to eliminate the possibility of friction distorting the LVDT response. To accomplish this, the metal push rods have been double heat treated and machined to ensure straightness. The push rods are designed for a clearance of 0.008 inches between one another.

To allow for alignment during setup of microwave compatible dilatometer 230 two electrical circuits have been designed such that if contact is made between push rods a signal is transmitted to a voltmeter. The continuity of the push rods can be monitored during setup and during operation.

Microwave compatible dilatometer 30, shown in FIG. 1 and microwave compatible dilatometer 230, shown in FIG. 2 have a range of +0.5 in. and a sensitivity of 0.0001 in. or 0.01% for a sintering sample having an overall vertical dimension of 1 in. Both microwave compatible dilatometer 30, shown in FIG. 1 and microwave compatible dilatometer 230, shown in FIG. 2 can follow the entire course of sintering of a sample from the initial thermal expansion of the green part to the final densification and thermal contraction of the sample during the sintering cycle without leaking microwaves outside microwave heating device 20 and 220.

While there has been shown and described what is at present considered the preferred embodiment of the invention, it will be obvious to those skilled in the art that various changes and modifications may be made therein without departing from the scope of the invention as defined by the appended claims.

What is claimed is:

1. An apparatus for measuring and monitoring a change in the dimension of a sample being heated by microwave energy comprising:
   a microwave heating means for heating a sample by microwave energy, said sample having a dimension, said microwave heating means being a microwave furnace;
   a microwave compatible dilatometer means for measuring and monitoring a change in the dimension of a sample being heated by microwave energy without leaking microwaves out of said microwave heating means, said microwave compatible dilatometer comprising a linear variable differential transducer, said microwave heating means having an aperture through which a movable sample contact means extends, said movable sample contact means being in contact with a sample for transferring the dimensional change of a sample for measuring and monitoring the dimensional change of a sample, said movable sample contact means being adapted to transfer a change in dimension of a sample contained within said microwave heating means to said linear variable differential transducer, said movable sample contact means having a diameter less than said diameter of said aperture in said microwave heating means being adapted to receive said movable sample contact means, said diameter of said aperture being sufficiently small to prevent leakage of microwaves from said microwave heating means through said aperture with said movable sample contact means extending from said linear variable differential transducer through said aperture to said sample, said microwave compatible dilatometer means being adapted to said microwave heating means and contacting said sample contained within said microwave heating means; and
   a temperature monitoring means for monitoring and measuring the temperature of a sample being heated by microwave energy, said temperature monitoring means comprising an optical window in said microwave heating means in combination with an optical pyrometer for viewing a sample.

2. An apparatus in accordance with claim 1 wherein said movable sample contact means is made from a non-microwave conducting material.

3. An apparatus in accordance with claim 1 wherein said dilatometer is shielded from microwave radiation by a shielding means.

4. An apparatus for detecting and measuring a change in the dimension of a sample being heated by microwave energy comprising
   a microwave heating means for heating a sample by microwave energy, said sample having a dimension, said microwave heating means having a aperture; and
   a microwave compatible dilatometer means for detecting and measuring a change in said dimension of said sample being heated by microwave energy comprising a linear variable differential transducer, an outer push rod, an inner push rod means, and a temperature monitoring means for monitoring and measuring the temperature of said sample being heated by microwave energy, and being adapted to receive said outer and inner push rod means and said temperature monitoring means through said aperture of said microwave monitoring means, said outer and inner push rod means being concentric axial hollow rods, said outer push rod means being adapted to maintain a point of reference of said sample to said variable differential transducer, said outer push rod means having a microwave shielding means, said outer push rod means being arranged concentrically around said inner push rod means, said inner push rod means being adapted to transfer a change in dimension of said sample contained within said microwave heating means to said linear variable differential transducer, said inner push rod means having a microwave shielding means, said inner push rod means being arranged concentrically around said temperature monitoring means.

5. An apparatus in accordance with claim 4 wherein said microwave heating means is a microwave furnace.

6. An apparatus in accordance with claim 4 wherein said temperature monitoring means is a thermocouple.

7. An apparatus in accordance with claim 4 wherein said
   outer push rod means and said inner push rod means have an upper portion and a lower portion, said upper portion of said outer push rod means and said inner push rod means is made of a ceramic material which does not significantly couple to microwaves of said microwave heating means, said lower portion of said outer push rod means and said inner push rod mans is made of metal, said upper portion of said inner push rod means is connected to a first cap, said first cap being in contact with a first surface of said sample, said lower portion of said inner push rod means is connected to said linear variable differential transducer, said upper portion of said outer push rod means is connected to a second cap, said second cap being in contact with a second surface of said sample, said second surface of said sample being parallel with said first surface of said sample, said first cap and said second cap being made from a ceramic material which does not significantly couple to microwaves of said microwave heating means.

8. An apparatus in accordance with claim 4 wherein said first cap and said second cap are made a material selected from the group consisting of boron nitride, aluminum oxide and combination thereof.

9. An apparatus in accordance with claim 4 wherein said upper portion of said outer push rod means and of said inner push rod means is made from material selected from the group consisting of boron nitride, aluminum oxide and combination thereof.

10. An apparatus for measuring and monitoring a change in the dimension of a sample being heated by microwave energy comprising:
    a microwave heating means for heating a sample by microwave energy, said sample having a dimension, said microwave heating means being a microwave furnace;
    a microwave compatible dilatometer means for measuring and monitoring a change in the dimension of a sample being heated by microwave energy without leaking microwave out of said microwave heating means, said microwave compatible dilatometer comprising a linear variable differential transducer, said microwave heating means having an aperture through which a movable sample contact means extends, said movable sample contact means being in contact with a sample for transferring the dimensional change of a sample for measuring and monitoring the dimensional change of a sample, said movable sample contact means being adapted to transfer a change in dimension of a sample contained within said microwave heating means to said linear variable differential transducer, said movable sample contact means having a diameter less than said diameter of said aperture in said microwave heating means being adapted to receive said movable sample contact means, said diameter of said aperture being sufficiently small to prevent leakage of microwaves from said microwave heating means through said aperture with said movable sample contact means extending from said linear variable differential transducer through said aperture to said sample, said microwave compatible dilatometer means being adapted to said microwave hating means and contacting said sample contained within said microwave heating means; and a temperature monitoring means for monitoring and measuring the temperature of a sample being heated by microwave energy, said temperature monitoring means comprising a thermocouple.

11. An apparatus in accordance with claim 10 wherein said movable sample contact means is made from a non-microwave conducting material.

12. An apparatus in accordance with claim 10 wherein said dilatometer is shielded by microwave radiation by a shielding means.

* * * * *